(12) United States Patent
Lee et al.

(10) Patent No.: US 10,041,045 B2
(45) Date of Patent: Aug. 7, 2018

(54) MICROFLUIDIC THREE-DIMENSIONAL OSTEOCYTE NETWORK RECONSTRUCTED WITH MICROBEADS AS SCAFFOLD

(71) Applicants: THE TRUSTEES OF THE STEVENS INSTITUTE OF TECHNOLOGY, Hoboken, NJ (US); HACKENSACK UNIVERSITY MEDICAL CENTER, Hackensack, NJ (US)

(72) Inventors: Woo Young Lee, Lyndhurst, NJ (US);
Yexin Gu, North Bergen, NJ (US);
Qiaoling Sun, Secaucus, NJ (US);
Wenting Zhang, Kearny, NJ (US);
Jenny Zilberberg, Yardley, PA (US)

(73) Assignees: HACKENSACK UNIVERSITY MEDICAL CENTER, Hackensack, NJ (US); THE TRUSTEES OF THE STEVENS INSTITUTE OF TECHNOLOGY, Hoboken, NJ (US)

( * ) Notice: Subject to any disclaimer, the term of this patent is extended or adjusted under 35 U.S.C. 154(b) by 0 days.

(21) Appl. No.: 14/490,847

(22) Filed: Sep. 19, 2014

(65) Prior Publication Data
US 2015/0086993 A1    Mar. 26, 2015

Related U.S. Application Data

(60) Provisional application No. 61/880,305, filed on Sep. 20, 2013.

(51) Int. Cl.
*C12N 5/077*      (2010.01)
*C12M 1/00*      (2006.01)
(Continued)

(52) U.S. Cl.
CPC .......... *C12N 5/0654* (2013.01); *C12M 23/16* (2013.01); *C12M 25/16* (2013.01); *C12M 29/04* (2013.01);
(Continued)

(58) Field of Classification Search
CPC ............. C12N 5/0654; C12N 2506/13; C12N 2531/00; C12N 2533/18; G01N 33/5044;
(Continued)

(56) References Cited

U.S. PATENT DOCUMENTS 7,670,797 B2    3/2010    Vacanti et al.
2013/0143230 A1    6/2013    Tolias et al.

OTHER PUBLICATIONS

Boukhechba et al. Human Primary Osteocyte Differentiation in a 3D Culture System. Journal of Bone and Mineral Research (2009), v24(11), p. 1927-1935.*
(Continued)

*Primary Examiner* — Sean C. Barron
(74) *Attorney, Agent, or Firm* — McCarter & English, LLP; Beverly W. Lubit

(57) ABSTRACT

A bed of microbeads is used as a foundation for reconstructing a three-dimensional osteocyte network by culturing osteocytes within the bed. The osteocytes are cultured such that they form a network among the microbeads that is capable of simulating the osteocyte network of natural bone. The osteocytes are cultured in a microfluidic device adapted for the purpose.

5 Claims, 5 Drawing Sheets

(51) Int. Cl.
  *C12M 1/12*    (2006.01)
  *C12M 3/06*    (2006.01)
  *G01N 33/50*   (2006.01)

(52) U.S. Cl.
  CPC ..... *G01N 33/5026* (2013.01); *G01N 33/5044* (2013.01); *C12N 2531/00* (2013.01); *C12N 2533/54* (2013.01)

(58) Field of Classification Search
  CPC ........... G01N 33/5023; G01N 33/5026; C12M 23/16; C12M 25/02; C12M 25/16
  USPC ...................... 435/6.12, 29, 297.1, 377, 6.13
  See application file for complete search history.

(56) References Cited

OTHER PUBLICATIONS

Osteoblasts (2005; date from Internet Archive). In Wheeless' Textbook of Orthopaedics.*
Jang et al. Development of an osteoblast-based 3D continuous-perfusion microfluidic system for drug screening. Anal Bioanal Chem (2008), v390, p. 825-832.*
Celeromics product sheet for MCF cells + pub date (2010).
Friend et al., Fabrication of microfluidic devices using polydimethylsiloxane, Biomicrolluidics, 4, (2010).
Gu et al., Inkjet printed antibiotic- and calcium-eluting bioresorbable nanocomposite micropatterns for orthopedic implants, 8, (2012) 424-431.
Gu et al., Inkjet printed antibiotic- and calcium-eluting bioresorbable nanocomposite micropatterns, Third Thesinge Biofilm Meeting, Sep. 20-21, 2010, Thesinge, Netherlands (14 pages).
Gu et al., Inkjet-printed Drug-eluting Biodegradable Micropatterns for Rapid Wound Healing and Infection Prevention, 9th World Biomaterials Congress, Jun. 1-5, 2012, Chengdu, China (13 pages).
Harbeck, et al., Personalized treatment of early-stage breast cancer: Present concepts and Future Directions, Cancer Treatment Reviews, 36, (2010) 584-594.
Hartman, et al., Biofunctionalization of electrospun PCL-based scaffolds with perlecan domain IV peptide to create a 3-D pharmacokinetic cancer model, Biomaterials, 31, (2010) 5700-5718.
Hwang et al., Microfluidic Chip-Based Fabrication of PLGA Microfiber Scaffolds for Tissue Engineering, Langmuir, 24, (2008) 6845-6851.
Kim et al., A practical guide to microfluidic perfusion culture of adherent mammalian cells, Lab on a Chip, 7, (2007) 681-694.
Kirschner et al., A unique three-dimensional model for evaluating the impact of therapy on multiple myeloma, Blood, 112, (2008) 2935-2945.
Kuswandi et al., Optical sensing systems for microfluidic decives: a review, Analytica Chimica Acta, 601, (2007), 141-155.
Lee et al., Effects of *Staphylococcus epidermidis* on osteoblast cell adhesion and viability on a Ti alloy surface in a microfluidic co-culture environment, Acta Biomaterialia, 6 (2010) 4422-4429.
Lee et al., Microfluidic 3D Ossification Model for Implant-Related Infection, Stevens Conference on Bacteria-Materials Interactions, Jun. 9-10, 2011, Hoboken, New Jersey (19 pages).
Lee et al., Microfluidic 3D bone tissue model for high-throughput evaluation of wound-healing and infection-preventing biomaterials, Biomaterials, 33, (2012) 999-1006.
Lee et al., Microfluidic Ossified Tissue Model, Gordon Conference on Bones and Teeth, Jun. 19-24, 2011, Les Diablerets, Switzerland (1 page).
Lee, W., 3D Tissue Model for Orthopaedic Implant-Related Bacterial Infection, Seminar—New Jersey Dental School, Nov. 9, 2010 (31 pages).
Lee, W. et al., Bone-Like Materials Created by Biomimetic 3D Microfluidics, DFG-NSF Conference, Bioinspired Design and Engineering of Novel Functional Materials, Mar. 23-25, 2011, New York, New York, (13 pages).
Levenson et al., MCF-7: The First Hormone-responsive Breast Cancer Cell Line, Cancer Research, 57, (1997) 3071-3078.
Sanguinetti et al., hERG potassium channels and cardiac arrhythmia, Nature, 440, (2006) 463-469.
Song et al., An integrated microfluidic cell array for apoptosis and proliferation analysys induction of breast cancer cells, Biomicrofluidics, 4, (2010).

* cited by examiner

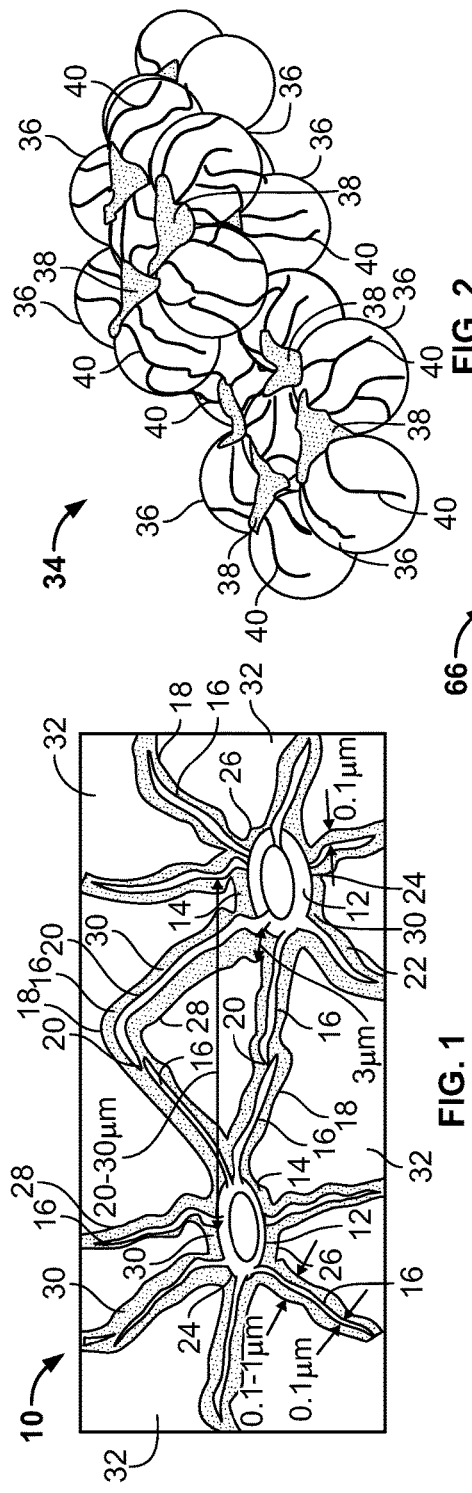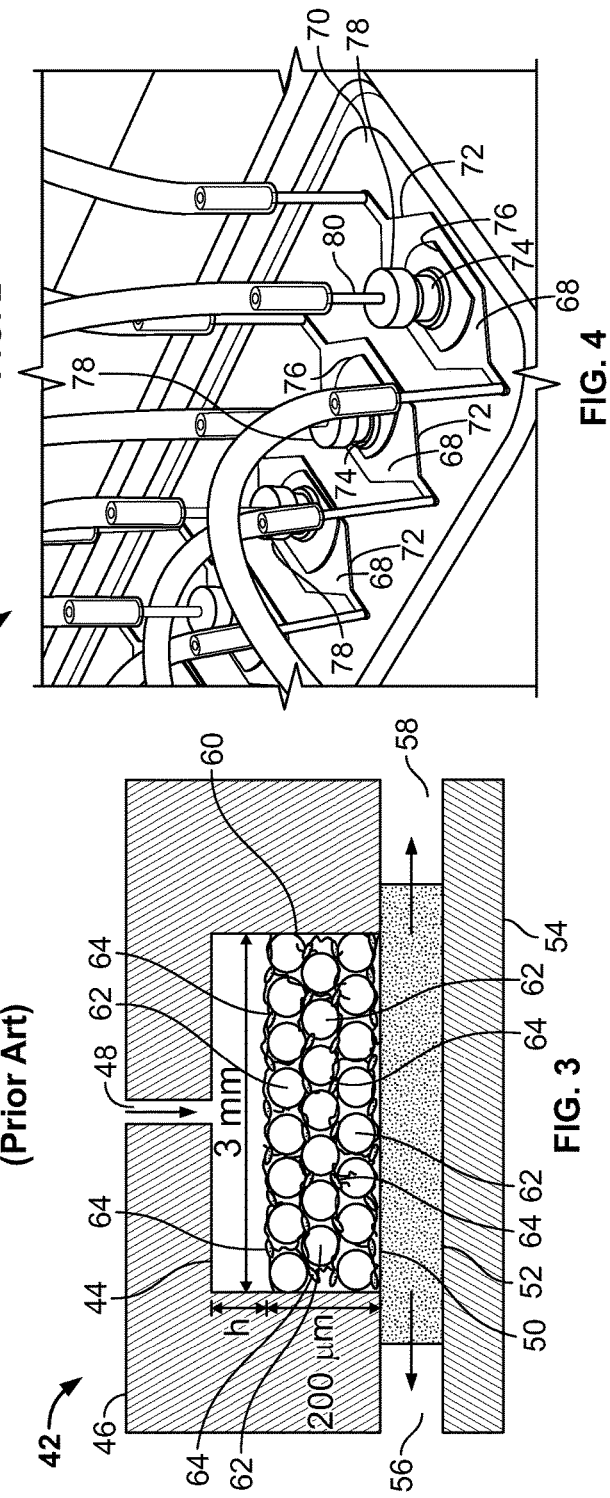

MICROFLUIDIC THREE-DIMENSIONAL OSTEOCYTE NETWORK RECONSTRUCTED WITH MICROBEADS AS SCAFFOLD

CROSS-REFERENCE TO RELATED APPLICATIONS

The present application claims the benefit of U.S. Provisional Patent Application No. 61/880,305, filed on Sep. 20, 2013, the disclosure of which is incorporated by reference herein in its entirety.

STATEMENT REGARDING FEDERALLY SPONSORED RESEARCH

Development of the present invention was sponsored in part by the National Science Foundation ("NSF") under Grant Numbers DMR-1005902 and DMR-1409779, and the National Institute of Arthritis and Musculoskeletal and Skin Diseases of the National Institutes of Health ("NIH-NIAMS") under Award Number R21AR065032. The U.S. Government may have certain rights to the disclosed invention.

FIELD OF THE INVENTION

The present invention relates to the construction of in vitro tissue models, more specifically methods and devices for in vitro culturing of bone tissue models comprising osteocyte 3D network.

BACKGROUND OF THE INVENTION

As master regulators of homeostatic bone remodeling, mature osteocytes embedded in the three-dimensional (3D) lacuna-canalicular network (3D-LCN) structure are known to sense local compressive strain and initiate strain-dependent new bone formation by osteoblasts, utilizing cytokines such as sclerostin and Dkk1 expressed by the osteocytes as major signaling molecules. For example, mouse ulna loading studies elegantly show that higher strain regions of the ulna bone result in less production of sclerostin and increased local osteogenesis at those regions.

Despite these important understandings, a significant challenge remains for in vivo studies of osteocytes due to the difficulty of accessing deeply embedded osteocytes in bone tissues. As yet, there is currently no in vitro model that is capable of reproducing the physiological phenotype and mechanotransduction function of osteocytes for routine use in biomedical research and preclinical drug evaluation. This problem may occur for several reasons: (1) the phenotypic function of primary osteocytes harvested from animal bones cannot be maintained during conventional two-dimensional (2D) culture; (2) commonly used osteocyte-like cell lines such as MLO-Y4 are sufficiently altered so that they do not express sclerostin at detectable levels; and (3) in vitro differentiation of osteoblasts into 3D mature osteocytes with network formation and sclerostin expression has not been realized.

A novel in vitro bone tissue model with a reconstructed 3D osteocyte network could be extremely useful for studying fundamental biological mechanisms associated with osteocytes as master regulators of bone remodeling. The model can be preliminarily validated by reconstructing the bone-like tissue with a 3D mouse osteocyte network and comparing it to the in vivo mouse data. Furthermore, the comparison could provide significant new insights and promote new developments in culturing primary human osteocytes and extending the model's capability for simulating human bone remodeling, including osteocyte-regulated bone formation and bone resorption. Operated at a microfluidic scale, such a human 3D bone tissue model may complement (or possibly replace) animal testing in preclinical evaluation of authentic human tissue response to drugs (e.g., sclerostin antibodies that are being actively pursued for treating the approximately 10 million osteoporosis patients in the U.S., and for treating bone metastases, which presently cause about 350,000 deaths every year in the U.S.

SUMMARY OF THE INVENTION

In a first aspect, the present invention comprises a method of culturing osteocytes in a microfluidic chamber. In an embodiment, a suspension of pre-osteocytes is mixed with microbeads, and the mixture is deposited in a microfluidic chamber to form a bed of closely-packed microbeads with pre-osteocytes distributed among the microbeads. In an embodiment, the bed is perfused with a culture medium such that the pre-osteocytes differentiate and develop into osteocytes. In an embodiment, the cultured osteocytes along with the close-packed microbeads form a bone-like tissue. In an embodiment, the microbeads have diameters such that interstitial spaces between adjacent microbeads may be occupied by no more than one of the cells. In an embodiment, the embedded cells form 3D network emulating the LCN structure in native bone tissues. In an embodiment, a drug or other biologically-active substance is included in the culture medium, and the effect of the drug or other biologically-active on the development of the bone-like tissue is assessed. In an embodiment, the microbeads include biphasic calcium phosphate. In an embodiment, the cells include pre-osteocytes and/or osteocytes.

In a second aspect, the present invention comprises a microfluidic device having a chamber defining an opening and having an inlet spaced away from the opening, a semipermeable barrier closing said opening, an impermeable substrate across the semipermeable barrier, and an outlet for collecting liquid passing through the semipermeable barrier and conveying the liquid away from the microfluidic device. In an embodiment, the microfluidic device includes a liquid-permeable bed of microbeads and cells within the chamber.

BRIEF DESCRIPTION OF DRAWINGS

For a more complete understanding of the present invention, reference is made to the following detailed description of exemplary embodiments considered in conjunction with the accompanying drawings, in which:

FIG. 1 is a schematic illustration of an osteocyte network in a lacunocanalicular structure;

FIG. 2 is a schematic illustration of a biomimetic assembly of a three-dimensional (3D) osteocyte network guided by closely-packed microbeads, according to an embodiment of the present invention;

FIG. 3 is a schematic illustration of a microfluidic culture device, according to an embodiment of the present invention;

FIG. 4 is a schematic illustration of an array of microfluidic culture devices, according to an embodiment of the present invention;

DETAILED DESCRIPTION OF THE INVENTION

Figure 5:
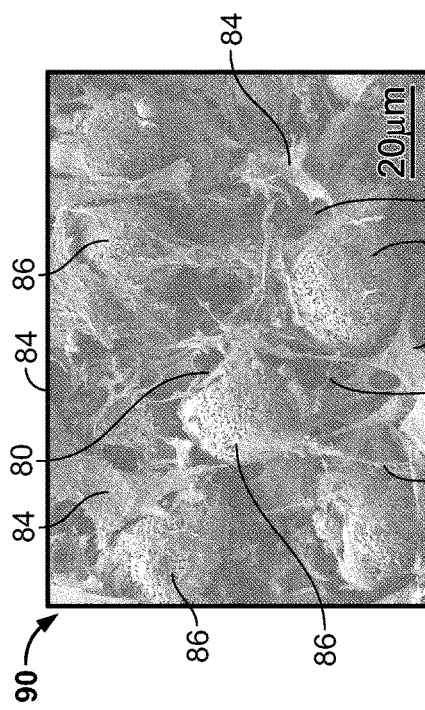
FIG. 5 is an image of a bone tissue model with cells and microbeads, according to an embodiment of the present invention.

Embodiments of the present invention provide a biomimetic approach to emulate the physiologically-relevant microscale dimensions of three-dimensional ("3D") lacuno-canalicular structures ("3D-LCN") that can be subjected to long-term perfusion culture. In this approach, osteocytes and/or osteocyte precursors are assembled with microbeads within the physical confines of a microfluidic culture chamber. In the microfluidic environment, the model of the present invention allows compressive loading to be applied to the reconstructed 3D osteocyte networks. The microfluidic environment also allows for the reproduction of the compressive strain-sclerostin expression relationship as a means of validating the functionality of the reconstructed 3D osteocyte network. Devices and methods according to embodiments of the present invention may be used to assess the effectiveness of bioactive substances on the growth or regeneration of bone tissues, or as part of integrated microfluidic systems to assess the safety and effectiveness of medical treatments. Suitable integrated microfluidic systems are disclosed in U.S. Patent Application Publication No. 2013/0143230 by Tolias et al., which is incorporated by reference herein in its entirety.

Osteocytes are the most abundant cells (more than 90%) that reside in mineralized extracellular matrix ("ECM") cavities in bones. Such cavities are referred to as "lacunae". As illustrated in FIG. 1, which shows typical dimensions of internal structures of a portion 10 of a cortical bone, neighboring osteocytes 12 in lacunae 14 in the extracellular matrix ("ECM") 32 of the bone 10 are interconnected by tens of dendritic processes 16 extending from the osteocytes 12 through smaller channels 18 ("canaliculi") in all directions. Adjacent dendritic processes 16 form gap junctions 20. The extracellular spaces 22 between the osteocyte cell surface 24 and the lacunar and canicular walls 26, 28 are filled with matrix proteins 30 such as proteoglycans and glycosaminoglycans with an effective pore size of about 10 nm. Osteocytes 12 in this 3D cellular network are known to function as master regulators of homeostatic bone remodeling. They have also been implicated for regulative contributions in metabolic demands for minerals, and for hematopoiesis.

As illustrated in FIG. 2, an embodiment 34 of the present invention uses microbeads 36 to mimic the ECM geometry and mechanical support function of the 3D-LCN, to guide the re-establishment of 3D cellular networks of osteocytes 38. In an embodiment, the microbeads 36 comprise biphasic calcium phosphate ("BCP"). The microbeads 36 are selected to: (1) spatially distribute osteocyte cell bodies 38 into the interstitial spaces (not visible in FIG. 2) between the microbeads 36 with one cell 38 occupying each interstitial site, while allowing the cells 38 to develop dendritic processes 40 and gap junctions (not shown) with neighboring cells 38 with the physiologically relevant lacuna and interlacunar dimensions; and (2) provide a mechanically stable framework to maintain the microscale geometry and dimensions of the 3D cellular network during perfusion culture. Microbeads 36 may be made of a number of different materials, and are commercially available with nominal diameters in the range of about 10 μm to about 1000 μm.

The diameter of BCP microbeads used in the reconstructed tissue of embodiments of the present invention can be selected according to the osteocyte diameter and intercellular space that varies between species. For close-packed microbeads, the diameter of interstitial sites (d') and the distance between interstitial sites (d) are:

$$d' \approx 0.4D \qquad \text{Eq. 1}$$

$$d = D \qquad \text{Eq. 2}$$

where D is the diameter of microbeads. Therefore, for mouse osteocyte cells (e.g., cell lines MLO-Y4 or MLO-A5) with a typical diameter of 8-10 μm, microbeads with diameters in the range of about 20 to about 25 μm may be selected to: (1) allow a single cell to be placed within the interstitial site that is sufficiently large (d'=8-10 μm), for occupation by one cell, but too small for occupation by more than one cell; (2) mitigate the proliferation of the cell placed in the interstitial site due to the physical confinement by the interstitial site; and (3) control the cell-to-cell distance to that of d (i.e., about 20-25 μm). In an embodiment, BCP is chosen as the microbead material, since BCP is known to facilitate mineral deposition by early and late osteoblastic cells through controlled release of calcium ions. Other suitable microbead materials may be preferred by others having ordinary skill in the relevant arts.

FIG. 3 is a schematic illustration of a microfluidic device 42 of the present invention suitable for use in microfluidic culturing of osteocytes. The device comprises a chamber 44 formed within a polymer block 46 (e.g., polydimethylsiloxane ("PDMS")). An inlet 48 is provided in the polymer block 46 for hydraulically connecting the chamber 44 to an external device (not shown). The chamber 44 has an opening 50 spaced away from the inlet 48 which is closed by a semipermeable barrier 52, and an impermeable substrate 54 (e.g., a glass slide) is provided such that the semipermeable barrier 52 is between the substrate 54 and the chamber 44. The semipermeable barrier 52 allows liquids to pass through the semipermeable barrier 52 into outlets 56, 58 formed by or in the impermeable substrate 54, which hydraulically connect the device 42 to the external environment (not shown). A bed 60 of BCP microbeads 62, with cells 64 distributed among the microbeads 62, is provided within the chamber 44, with the inlet 48 offset from the bed 60 by a distance h.

FIG. 4 is a photographic image of a microfluidic device 66 consisting of multiple microfluidic culture devices 68 of the same general type as device 42 of FIG. 3. Using techniques known in the art, and following procedures such as those described in the aforementioned U.S. Patent Application Publication No. 2013/0143230, soft-lithography was used to fabricate a PDMS layer 70 containing hexagonal patterns 72 having dimensions of 6 mm by 12 mm and 200 μm thick. Holes (not visible in FIG. 4) having diameters of about 3 mm were then punched in the middle of the patterns 72 to form culture chambers 74. The PDMS layer 70 was then bonded to a glass slide (not visible in FIG. 4) while placing a filter membrane layer 76 (MF-Millipore™) of 4 mm in diameter and 200 μm in thickness between the PDMS layer 70 and the glass slide to serve as a semipermeable barrier 76. Beds of microbeads and cells (not show) were provided inside the chambers 74, and the chambers 74 were closed from the top with PDMS caps 78. Stainless steel tubes 80 were placed into the caps 78 to serve as inlets for culture media.

In a general embodiment of a method according to the present invention, a suspension of pre-osteocyte cells is suspended and mixed thoroughly with microbeads. A portion of the mixture is placed on the semipermeable barrier of a microfluidic culture device, such as the microfluidic culture devices 42, 66 of FIGS. 3 and 4. The cells are allowed to attach to the microbeads, and the cell/microbead construct is perfused with a culture medium. After culturing the cells for a set period, the microfluidic culture devices are disassembled and the cultured tissue/microbead construct is retrieved for examination or use. In some embodiments of the present invention, the culture medium includes one or more drugs or other biologically active compounds for assessment of their effects on the growth and development of osteocytes and bone-like tissues.

EXEMPLARY EMBODIMENTS

Exemplary embodiments of the present invention are presented below. These embodiments do not limit the scope of the invention, which includes numerous modifications and variations of the exemplary embodiments, as will be recognized by those having ordinary skill in the relevant arts.

Example 1

In an exemplary embodiment, spray-driedisintered BCP microbeads (CaP Biomaterials, LLC, East Troy, Wis.) were sieved to a size range according to the size and intercellular space of the subject osteocytes in authentic bones. For mouse osteocytic cell line MLO-Y4, with typical diameters of 8 to 10 μm, microbeads of 20 to 25 μm in diameter were used. The microbeads were then coated with a collagen solution. In the present exemplary embodiment, the microbeads were coated using a 10 mg/mL collagen/hexafluoroisopropanol solution. After sufficient time had elapsed to evaporate the hexafluoroisopropanol solvent (e.g., approximately one hour), the microbeads were washed with phosphate buffered saline (PBS).

The MLO-Y4 cells were cultured and expanded in collagen-coated flasks using alpha-minimum essential medium (α-MEM, Invitrogen, Carlsbad, Calif.), supplemented with 2.5% fetal bovine serum (FBS, ATCC), 2.5% calf serum (CS, ATCC) and 1% antibiotic solution (penicillin-streptomycin, MP Biomedicals, Solon, Ohio). The cells were then maintained at about 37° C., about 5% $CO_2$ and over 90% humidity, and subcultured when they reach about 80% confluence.

The cellular tissue was then allowed to reconstruct. After tissue reconstruction, the cells were suspended and mixed with the coated microbeads. In the present exemplary embodiment, the cells were suspended using trypsin, then mixed with BCP microbeads to final concentrations of $1 \times 10^7$ cells/mL and $1 \times 10^7$ microbeads/mL (i.e., cell/microbead ratio of 1:1). Referring again to FIG. 3, 10 μL of the mixture of cells 64 and microbeads 62 were added to the microfluidic chamber 44 to form a bed 60 of microbeads 62 having a thickness of about 200 μm. In the present exemplary embodiment, the cells were allowed to attach to the microbeads over a period of about 1 hour. The microfluidic chamber 44 was then sealed, and a culture medium (not shown) was perfused through the microfluidic chamber 44. In the present exemplary embodiment, culture media were applied to the microbead beds within separate chambers, prepared as described above, at respective flow rates of 1 μL/min and 5 μL/min. These flow rates are merely exemplary, and other flow rates may be envisioned and used in other embodiments of the present invention.

Following the aforesaid perfusion, the cells were further cultured within the microfluidic chamber by perfusion with a growth medium. In the present exemplary embodiment, growth culture was carried out for 3 days in α-MEM supplemented with 5% FBS, since FBS is known to help maintain the osteocytic phenotype of the cells.

After the growth culture, the resulting tissue construct of microbeads and cultured cells appeared as a monolith (see, e.g., the tissue construct 82 of FIG. 5). The tissue construct was fixed within the microfluidic chamber with a 4% formaldehyde/PBS solution, washed with PBS, and dehydrated using a 30% sucrose/PBS solution. The microfluidic chamber was then disassembled, and the tissue construct was embedded for frozen sectioning for preservation. The tissue construct was cross-sliced into 20 µm-thick sections, stained with DAPI (Invitrogen), and immediately examined under a fluorescent microscope. It was observed that osteocytes resided in the interstitial spaces between the microbeads, and were distributed throughout the tissue construct. More cells were observed on the upper surface of the tissue construct than within the tissue construct, which appeared to be a result of the proliferation and confluence of the osteocytes that are present on the surface of the tissue construct. In contrast, the proliferation of the cells trapped in the interstitial spaces between the microbeads appeared to have been hindered.

Figure 6:
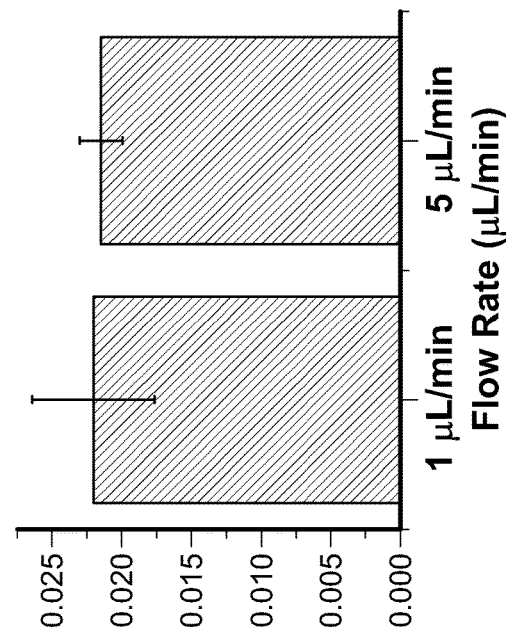
FIG. 6 is a scanning electron microscopic (SEM) image of a portion of a bone tissue model of the same general type as that of FIG. 5 using a mature osteocyte cell line MLO-Y4, according to an embodiment of the present invention.

Referring to FIG. 6, scanning electron microscope (SEM) analysis of the tissue construct, the tissue construct was fixed and dehydrated in diluted ethanol. Continuing to refer to FIG. 6, osteocyte cell bodies 84 were found to be attached to the surfaces of the microbeads 86. Each cell 84 included several dendritic processes 88 that extended through interstitial spaces (not shown), and connected with processes 88 from neighboring cells 84 which form gap junctions (not visible in FIG. 6), thereby forming a 3D osteocyte cellular network 90.

Figure 7:
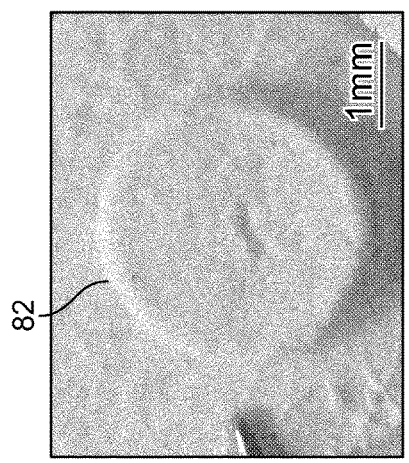
FIG. 7 is a bar chart illustrating the percentages of viable, injured, and dead MLO-Y4 cells in a bone tissue model, according to an embodiment of the present invention.

Cell viability in the tissue was determined by removing the cells from the tissue construct, staining the cells and measuring cell viability. In this exemplary embodiment, this process was carried out utilizing live/dead cell viability dye (Invitrogen) as stain, and quantitatively measuring cell viability through flow cytometry. These results were performed under triplication. As illustrated in FIG. 7, more than 90% of the cells were viable after 3-day culture under both 1 µL/min and 5 µL/min perfusion conditions.

Figure 8:
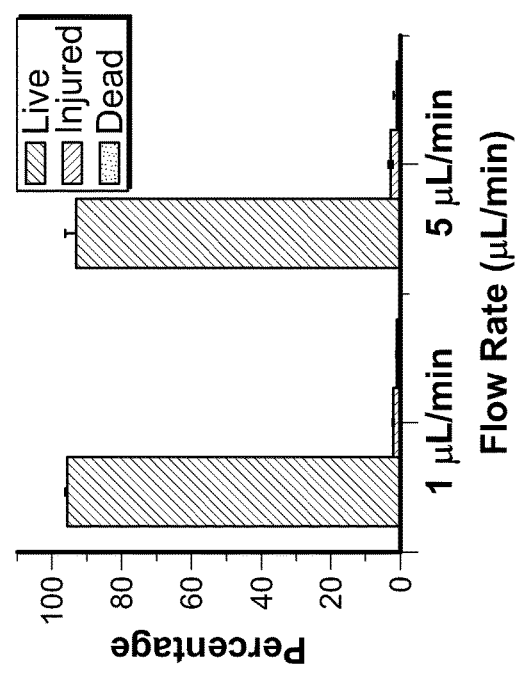
FIG. 8 is a bar chart illustrating the relative expression of Pdpn by MLO-Y4 cells in a bone tissue model at different culture medium flow rates, according to an embodiment of the present invention.

Osteocyte-specific gene Pdpn, which regulates osteocyte process growth, was examined using quantitative real-time polymerase chain reaction techniques (PCR). As illustrated in FIG. 8, Pdpn was highly expressed at both of the exemplary flow rates of culture medium. The high expression of Pdpn indicates that the MLO-Y4 cells retained their osteocytic phenotype in the 3D tissue construct.

Example 2

Figure 9:
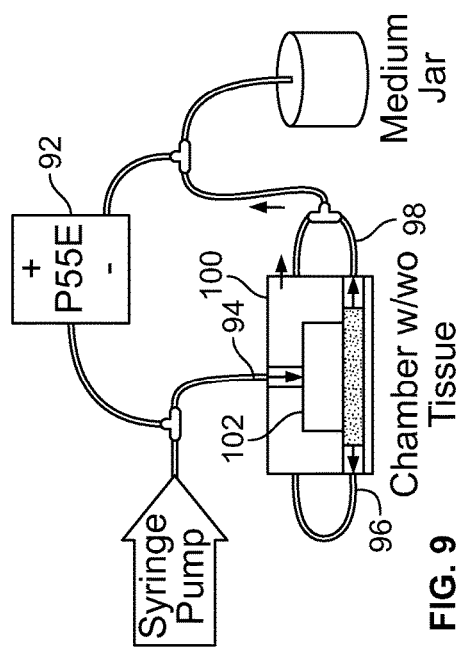
FIG. 9 is a schematic illustration of a system for monitoring pressure drops across a chamber of a microfluidic culture device, according to an embodiment of the present invention.

This second exemplary embodiment demonstrates the 3D morphological development, extracellular matrix production, and differentiation of early osteocytes of the MLO-A5 line entrapped in the tissue/microbeads construct during 3 weeks of perfusion culture in the microfluidic culture chamber.
Materials and Methods
BCP Microbeads Spray-dry/sintered BCP microbeads were purchased from CaP Biomaterials LLC (East Troy, Wis.). According to the supplier, the microbeads were composed of 68% of hydroxyapatite and 32% of β-tricalcium phosphate. The microbeads were sieved to a size range of 20-25 µm and coated with collagen type I (Sigma-Aldrich) using 10 mg/mL collagen/hexafluoroisopropanol solution for 2 hours. They were then washed with phosphate buffered saline (PBS) three times and stored for further use.
MLO-A5 Cell Culture The MLO-A5 post-osteoblast/pre-osteocyte cell line was a kind gift from Professor Lynda Bonewald (University of Missouri-Kansas City). Cells were maintained in collagen-coated flasks in α-MEM (Gibco) supplemented with 5% (v/v) fetal bovine serum (FBS, ATCC), 5% (v/v) calf bovine serum (CBS, ATCC) and 1% (v/v) penicillin-streptomycin (P/S, MP Biomedicals, Solon, Ohio) at 37° C. and 5% $CO_2$, and subcultured once until they reached about 80% confluence. Cells from passages 2 to 9 were used according to the exemplary culture and characterization methods described below.
Microfluidic 3D Culture of MLO-A5 Cells with BCP Microbeads MLO-A5 cells were suspended using trypsin and mixed thoroughly with BCP microbeads at concentrations of $1 \times 10^7$ cells/mL and $1 \times 10^7$ microbeads/mL to produce a cell/microbead ratio of 1:1. 10 µL of the mixture was placed using a micropipette onto the top of the membrane in each chamber of the microfluidic device of FIG. 4 to form tissue/microbead constructs having thicknesses of about 200 µm. After waiting for 2 hours to let the cells to attach to the microbeads, the microfluidic chambers were sealed from the top by inserting PDMS caps. The space between the bottom of the caps and the tissue sample surfaces was kept at about 1 mm. Culture medium flow was applied through stainless steel tubes inserted into the caps at the tops the chambers using syringe pumps. The tissue samples were cultured up to 21 days at a flow rate of 1 µL/min of osteogenic α-MEM supplemented with 10% (v/v) FBS, 50 µg/mL ascorbic acid (Sigma), 3 mM β-glycerophosphate (Sigma) and 1% (v/v) P/S.
Pressure Drop Measurement across the Tissue Models As shown in FIG. 9, the pressure drop (ΔP) across the tissue samples was measured using a pressure sensor (P55E, Validyne Engineering Corp., CA) that was connected between the inlet 94 and outlet tubing 96, 98 of the microfluidic culture device 100. The measurements were conducted at Days 1 and 3. ΔP across the empty chambers 102 and chambers 102 filled with only BCP microbeads (not shown) were also measure as controls. All measurements were triplicate (i.e., three separate culture chambers).
Live/Dead Cell Vitality Assay At Day 3, the microfluidic devices were disassembled to harvest the cultured tissues. Cells were trypsinized to detach them from the BCP microbeads and stained with the live/dead cell vitality dye (Invitrogen) following the manufacturers protocol. Cell viability was quantitatively measured by flow cytometry (Beckman Coulter FC500). A minimum of 10,000 events were acquired and analyzed using the CXP cytometer analysis software (Beckman Coulter).
Cell and Tissue Morphology Characterization At Day 3 and Day 21, the 3D tissues were harvested and fixed with 4% formaldehyde/PBS solution. They were then dehydrated in sequential ethanol solutions with increasing concentrations from 50% to 100%. Some samples were embedded in glycol methacrylate and cut into histological sections of 20 µm thickness. Several sections were stained with 4',6-diamidino-2-phenylindole (DAPI, Sigma-Aldrich) to examine cell distribution under fluorescent microscopy (Nikon Ti), while other sections were stained with either toluidine blue (Sigma) or hematoxylin & eosin (H&E, Sigma) to examine cell morphology and extracellular matrix production under an optical microscope. A portion of the dehydrated samples were gold-coated and directly visualized under a scanning electron microscope (SEM, Zeiss Auriga FIB-SEM, Zeiss NTS, Peabody, Mass.).

The remaining samples were further examined by micro-computed tomography (microCT, Scanco µCT 35, Bassersdorf, Switzerland) system. The scans were performed in air using 3.5 µm voxel size, 45 KVp, 0.36 degrees rotation step (180 degrees angular range), 400 ms exposure and 1 averaging frame per view. The Scanco µCT software (HP, DECwindows Motif 1.6) was used for viewing of images and 3D image reconstruction. After 3D image reconstruction, volumes were segmented using a global threshold of 0.5 mg/cc. Directly measured bone volume fraction (BV/TV), tissue mineral density (TMD), trabecular number (Tb.N), trabecular thickness (Tb.Th), trabecular separation (Tb.Sp), connectivity density, and structure model index (SMI) were calculated for the 3D tissue samples cultured for 3, 10, and 21 days.

Osteoblast and Osteocyte Specific Gene Expressions by Quantitative PCR

Total RNA from the MLO-A5 cells cultured in the tissue/microbeads constructs was isolated at Day 3, 10 and 21, using an RNA Mini kit (Ambion) following the manufacturer's protocol. 1 µg of the total RNA from each sample was used for cDNA synthesis. Briefly, (1) 3 µL of 10 mM Oligo-dT solution (Sigma) was added to 16.5 µL of the RNA solution, heated at 75° C. for 5 min and cooled on ice; (2) a total of 30 µL reaction solution was: (1) constituted by further adding 1 µL RNasin Ribonuclease Inhibitor (Promega Corp, Madison, Wis.), 1.5 µL dNTp (Promega), 2 µL Reverse Transcriptase (Promega), and 6 µL Reverse Transcriptase Buffer (Promega), (2) incubated at 37° C. for 1.5 h, (3) stopped at 95° C. for 3 min, and (4) kept on ice. A final volume of the 20 µL reaction solution that consists of 2 µL of the cDNA template, 1 µL of primer, 10 µL of PCR master mix (Taqman), and 7 µL of DEPC-treated water was prepared for quantitative RT-PCR assay (StepOnePlus, Applied Biosystems). All primers were purchased from Taqman. Amplification conditions were as follows: 95° C., 20 s; 95° C., 1 s, 60° C., 20 s, 40 cycles. The relative expression of targeted genes was normalized to the GAPDH gene and gene expression level of cells at Day 0 using the $2\text{-}\Delta\Delta C_t$ method except Sost, for which $2\text{-}\Delta C_t$ method was used. The primers used are summarized in Table 1. 2D cultures were performed as controls using a 96-well plate that was pre-coated with a layer of BCP microbeads.

TABLE 1

Primers used in quantitative PCR

| Target Gene | Taqman Gene Expression Primer | Amplicon Length |
|---|---|---|
| Alpl | Mm00475834_m1 | 65 |
| Col1a1 | Mm00801666_g1 | 89 |
| Pdpn (E11) | Mm01348912_g1 | 120 |
| Dmp1 | Mm01208363_m1 | 74 |
| Cox43 (Gja1) | Mm01179639_s1 | 168 |
| Sost | Mm00470479_m1 | 55 |

Statistics

All samples in the assays of live/dead viability, MicroCT and qPCR were performed in triplicates. One-way ANOVA followed by the Tukey's multiple comparison tests was performed for pressure drop measurement, MicroCT and qPCR results. Student's t-test was used to analyze the result of qPCR between 2D and 3D culture. $p<0.05$ was considered statistically significant.

Results

Estimated Perfusion Characteristics

The culture medium flow rate of 1 µL/min was used, resulting in an average residence time of about 30 seconds through the 200 µm-thick tissue samples, to mimic interstitial flow from Haversian canals to the deepest regions of osteons. The pressure drop across the 3D microbeads without cells and the local average wall shear stress on the microbead surface were estimated using the modified Kozeny equation (Eqs. 1 and 2) developed by Riefler et al. and applying the tube bundle theory (Eqs. 3 and 4):

$$\frac{\Delta p}{\Delta x} = 72\left(\frac{\mu v_0}{D^2}\right)\frac{(1-\varepsilon)^2}{\varepsilon^3} \quad \text{Eq. 3}$$

$$v_0 = \frac{Q}{\varepsilon A} \quad \text{Eq. 4}$$

$$\tau_w = \frac{\Delta p}{\Delta x A_{VS}} \quad \text{Eq. 5}$$

$$A_{VS} = \frac{6(1-\varepsilon)}{D} \quad \text{Eq. 6}$$

where $\Delta P$ is the pressure drop across the thickness of the structure ($\Delta x \approx 200$ µm), $\varepsilon$ is the void fraction (about 0.3 for close packing), D is the mean diameter of microbeads (22.5 µm), µ is the viscosity of the medium, $v_0$ is the superficial velocity, Q is the volumetric velocity of culture medium, A is the cross-sectional area of the culture chamber, $\tau_w$ is the wall shear stress on the microbead surface, and $A_{VS}$ is the volumetric surface of the whole structure. Using these equations, $\Delta P$ and $\tau_w$ were estimated to be about 3.2 Pa and about 0.1 Pa, respectively, for the closed packed microbeads assembly.

Figure 10:
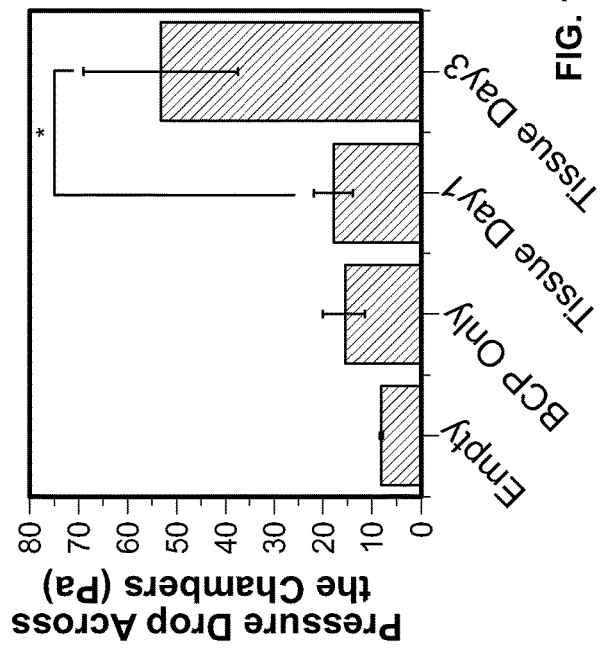
FIG. 10 is a bar chart of pressure drops across a microfluidic culture device under different conditions with pre-osteocyte cell line MLO-A5 culture, according to an embodiment of the present invention, wherein the asterisk (*) indicates statistically significant ($p<0.05$) differences between charted values.

In comparison, the measured $\Delta P$ value was 8.2 Pa for closely packed BCP particles in the absence of cells (see FIG. 10), which matched well with the theoretically predicted value of 3.2 Pa. In the presence of cells as well as increasing culture time, $\Delta P$ increased from 8.2 Pa to 10.5 Pa at Day 1 and 49 Pa at Day 3. The results suggested that $\varepsilon$ was decreased: (1) as a result of the cells occupying the interstitial sites between the microbeads and (2) more significantly due to newly produced extracellular matrix filing the rest of the interstitial spaces. The pressure drop of 49 Pa was associated with the porosity $\varepsilon$ of about 0.17 (Eqs. 3 and 4) and was expected to produce the wall shear stress of 1.1 Pa (Eqs. 5 and 6). This value is within the range of the shear stress that osteocytes are expected to experience in vivo during mechanical loading. However, with further increases in culture time, the pressure drop and shear stress are expected to be higher.

3D Osteocyte Network Formation

Figure 12:
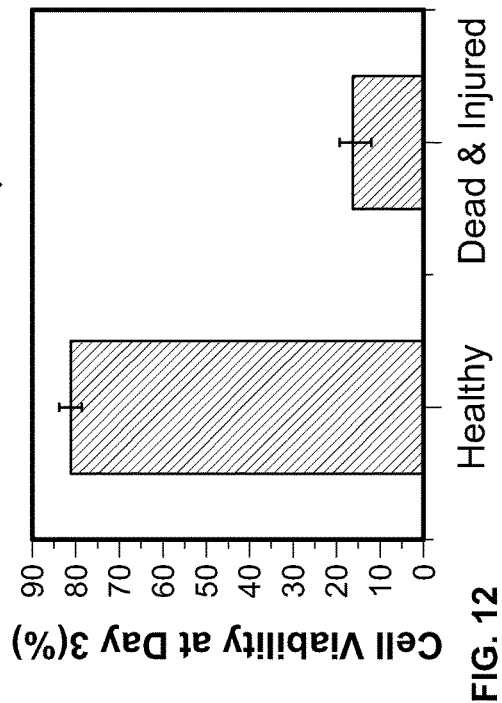
FIG. 12 is a bar chart of the numbers of healthy, injured, and dead cells in a bone tissue model, according to an embodiment of the present invention.
Figure 11:
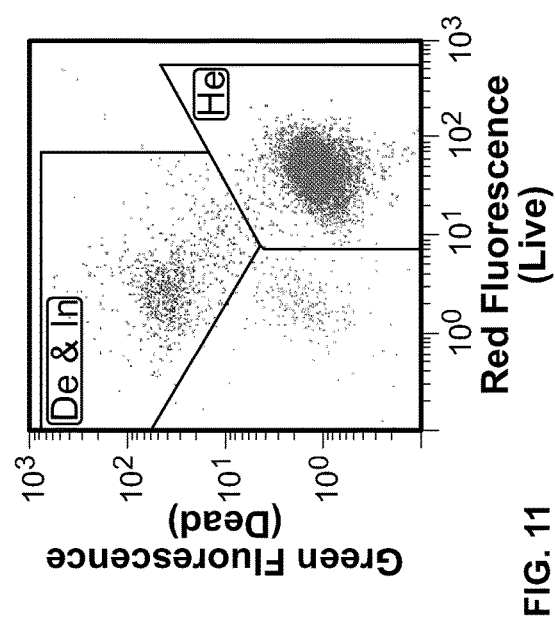
FIG. 11 is a plot of flow cytometry result showing healthy, injured, and dead MLO-A5 cells in a bone tissue model, according to an embodiment of the present invention.

A mechanically integrated structure of MLO-A5 cells and microbeads was obtained after 3 days of culture. The tissue samples were dismantled by trypsin and the released cells were collected for flow cytometry. As shown in FIGS. 11 and 12, healthy cells ("He") showed strong red and weak green fluorescence (81±2.4% of the cells). Dead and injured cells ("De & In") showed reduced red and strong green fluorescence (15.7±3.7%). Also, some debris of the BCP microbeads was detected as negative in both green and red fluorescence (about 3%).

Histological analysis of the 3D tissues stained with DAPI showed that cells occupied interstitial sites of microbeads, and were distributed throughout the 200 µm-thick samples. The interstitial occupancy by the cells was estimated to be about 80% based on cross-sectional images. Cross-sectional views with toluidine blue staining and top SEM views showed that the osteocyte-like cells attached to the microbeads, grew processes and extended their processes to neighboring cells to form gap-junctions in all directions. Taken together, the results show that the 3D cellular network could be formed upon 3 days of culture.

3D Tissue Characteristics after 21-Day Culture

Over the 21-day culture period, the cells produced significant amounts of ECM as previously described and became further embedded, as shown by H&E staining and SEM imaging. Also, SEM imaging showed that the cells became more elongated and stellate in their shape and formed tens of processes per cell, exhibiting characteristic morphological features of osteocytes. Moreover, the cells that were embedded in the interstitial space did not proliferate.

The Micro CT images of the tissue samples confirmed that tissues mineralized and became denser and more connective over time. As summarized in Table 2, the bone volume ratio (BV/TV) at Day 10 and Day 21 were 10% and 17% greater than at Day 3, respectively. Meanwhile, all other calculated parameters showed similar and consistent trends with respect to increased density and connectivity of the tissue samples.

TABLE 2

Micro CT results for the 3D tissue samples.

|  | Day 3 | Day 10 | Day 21 |
|---|---|---|---|
| BV/TV | 0.132 ± 0.0371 | 0.229 ± 0.0238* | 0.294 ± 0.0173* |
| TMD (mg) | 673 ± 2.27 | 687 ± 6.55* | 700 ± 2.03* |
| Tb.N (1/mm) | 31.0 ± 5.70 | 41.0 ± 4.15 | 47.0 ± 0.566* |
| Tb.Th (mm) | 0.00910 ± 0.0003 | 0.0104 ± 0.0007* | 0.0110 ± 0.0004* |
| Tb.Sp (mm) | 0.0334 ± 0.0067 | 0.0246 ± 0.0030 | 0.0208 ± 0.0004* |
| Conn-Dens. (1/mm$^3$) | 25594 ± 13624 | 57742 ± 10091* | 83023 ± 2994* |
| SMI | 3.10 ± 0.244 | 2.44 ± 0.251* | 1.86 ± 0.206* |

*$P < 0.05$ vs. Day 3

Osteocytic Development

Figure 14:
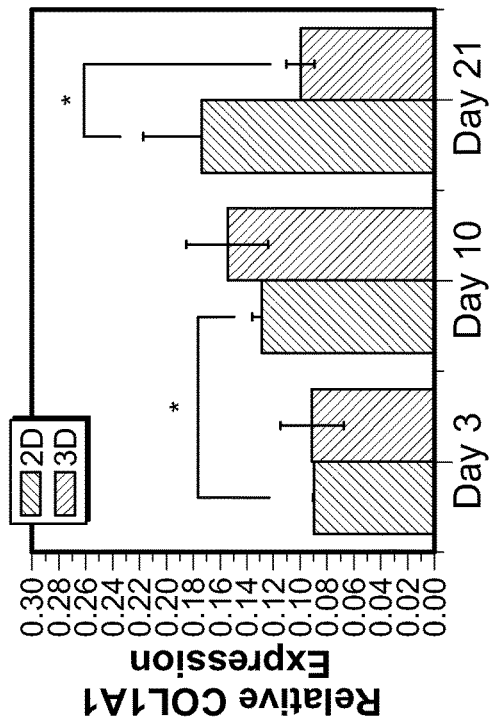
FIG. 14 is a bar chart of relative COL1A1 expression after different culturing periods for MLO-A5 cells cultured in a bone tissue model according to an embodiment of the present invention, wherein the asterisks (*) indicate statistically significant ($p<0.05$) differences between charted values.
Figure 13:
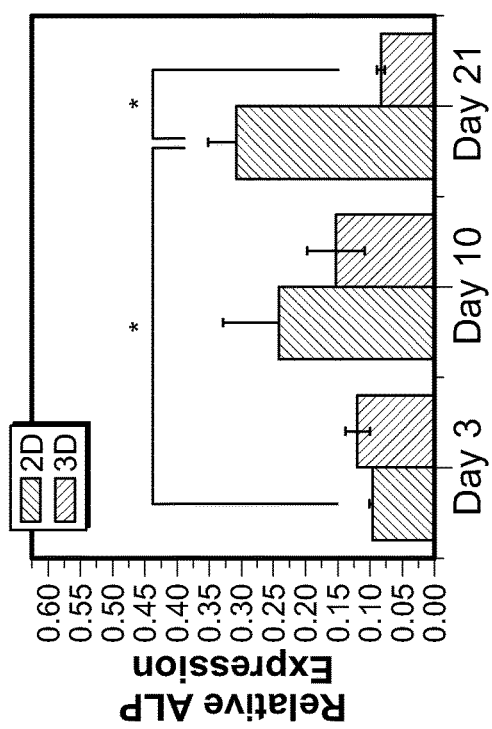
FIG. 13 is a bar chart of relative ALP expression after different culturing periods for MLO-A5 cells cultured in a bone tissue model according to an embodiment of the present invention, wherein the asterisks (*) indicate statistically significant ($p<0.05$) differences between charted values.

Osteoblast-specific genes (Alpl and Col1a1), osteoblast-to-osteocyte transition genes (E11 and Dmp1), gap-junction component protein gene (Cox43), and mature osteocyte-specific gene (Sost) were examined as a function of culture time. As shown in FIGS. 13 and 14, bath Alpl and Col1a1 gene expressions increased with time in 2D well-plate cultures while gene expression in the 3D tissues did not show similar trends. Despite having similar expression levels at Day 3 in comparison to 2D cultures, Alpl and Col1a1 expressions in 3D tissues were significantly down-regulated by factors of 3.7 and 1.7, respectively, after 21 days.

Figure 15:
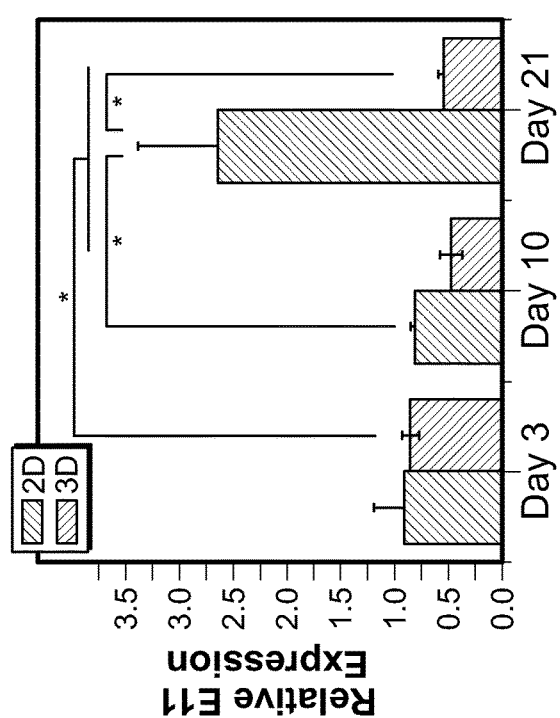
FIG. 15 is a bar chart of relative E11 expression after different culturing periods for MLO-A5 cells cultured in a bone tissue model according to an embodiment of the present invention, wherein the asterisks (*) indicate statistically significant ($p<0.05$) differences between charted values.
Figure 17:
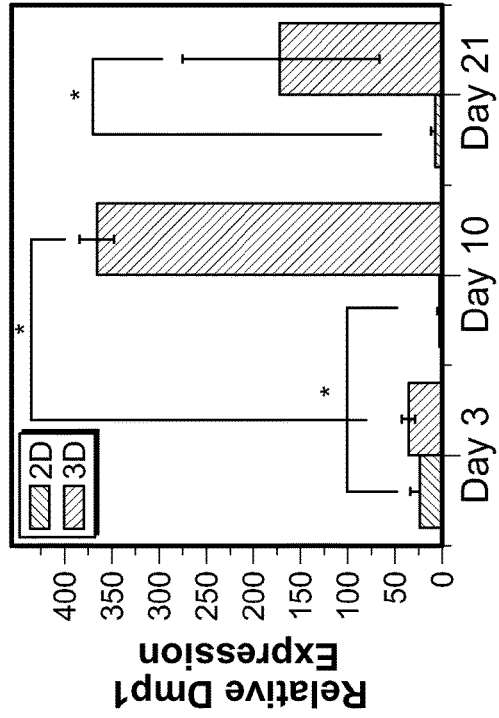
FIG. 17 is a bar chart of relative Dmp1 expression after different culturing periods for MLO-A5 cells cultured in a bone tissue model according to an embodiment of the present invention, wherein the asterisks (*) indicate statistically significant ($p<0.05$) differences between charted values.
Figure 16:
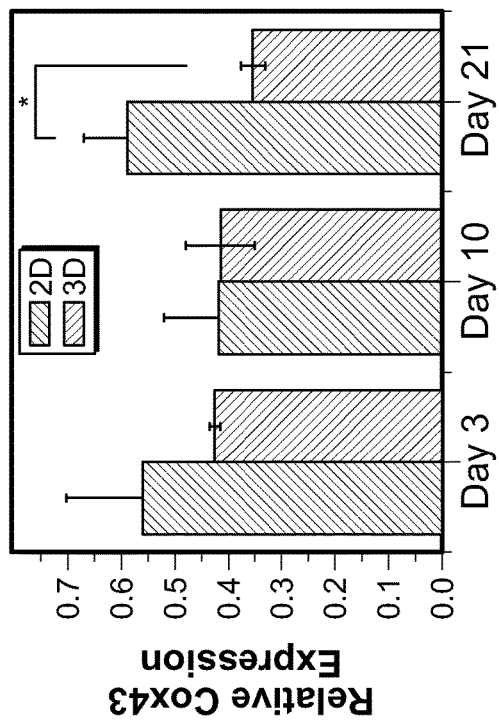
FIG. 16 is a bar chart of relative Cox43 expression after different culturing periods for MLO-A5 cells cultured in a bone tissue model according to an embodiment of the present invention, wherein the asterisks (*) indicate statistically significant ($p<0.05$) differences between charted values.

The expressions of early osteocyte-specific genes (E11 and Cox43) showed remarkable differences between 2D and 3D cultures (FIGS. 15 and 16). Specifically, during the 21-day culture period, E11 was up-regulated in 2D but down-regulated in 3D, which rendered a 2D/3D expression ratio of 5.1 at Day 21. The expression of Cox43, a gene that encodes Gap junction alpha-1 protein (Gja1), did not show significant difference between 2D and 3D by Day 10. However, at Day 21, its expression was significantly lower in 3D than in 2D. The expression of DMP1, another osteocyte-specific marker, started at similar levels between 2D and 3D at Day 3, but the expression was strongly enhanced in 3D with time whereas the cells significantly lost the expression in 2D. As a result, the Dmp1 expression in 3D was 21 times higher than that in 2D by Day 21 (FIG. 17).

Figure 18:
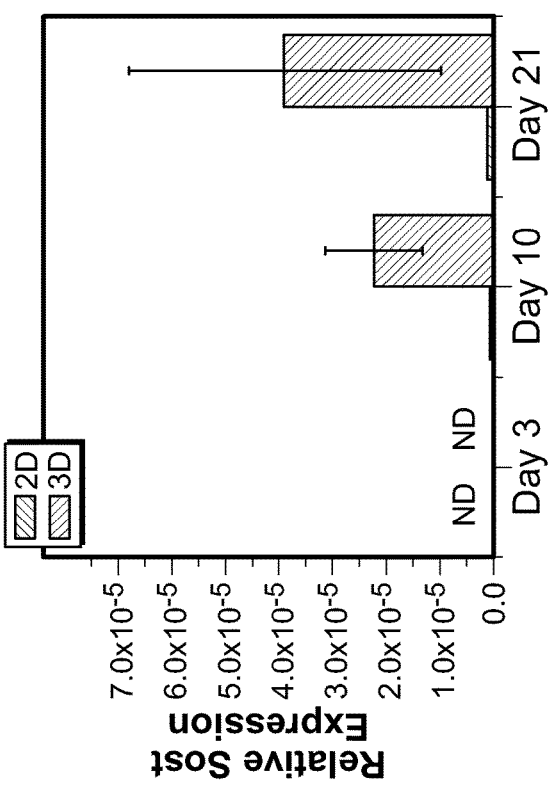
FIG. 18 is a bar chart of relative Sost expression after different culturing periods for MLO-A5 cells cultured in a bone tissue model according to an embodiment of the present invention, wherein the asterisks (*) indicate statistically significant ($p<0.05$) differences between charted values.

The late osteocyte-specific gene expression, Sost, was not detected in both 2D and 3D at Day 3 (FIG. 18). At Day 10 and 21, the Sost expression remained very low or undetectable in 2D. In contrast, the expression significantly increased with time in 3D with the expression elevated by two orders of magnitude by Day 21.

Example 3

Several iterative experiments were performed with primary mouse osteocytes, using the reconstruction strategy established with MLO-A5 cells, discussed in Example 2, above. Long bones of 20-week-old mice were harvested, cleaned, diced into small pieces of 1-2 mm long and 0.5 mm wide, and digested nine times using collagenase solutions. Cells that were immediately released from the bone pieces ("digested cells") did not adhere and were dead by Day 7. In contrast, cells that were gradually migrated out of the bone chips over 2 days ("outgrown cells") were viable over a few weeks. There were initially round-shaped, but became adherent and began to develop processes by Day 4. At this time, 88% of these cells were stained as Alp-negative and Sost-positive, and were therefore identified as osteocytes. After Day 7, it appeared that some of the outgrown cells were re-differentiating to become osteoblastic and proliferative. Outgrown cells were released from well plates using trypsin and then assembled with BCP microbeads into the perfusion culture device. About 30% of the interstitial spaces were observed to be occupied by the cells. The results clearly suggest the feasibility of reconstructing the 3D cellular network with primary osteocytes.

It should be understood that the embodiments of the invention described herein are merely exemplary and that a person skilled in the art may make many variations and modifications without departing from the spirit and scope of the invention. All such variations and modifications are intended to be included within the scope of the invention as defined in the appended claims.

We claim:

1. A method of forming a three-dimensional (3D) osteocyte network in vitro by culturing osteocytes in a microfluidic chamber, comprising the steps of:
   (a) mixing two or more cells with two or more microbeads in a ratio of about 1:1 to form a mixture including the cells and the microbeads, wherein the cells include an osteocyte, a pre-osteocyte or both, and further wherein the microbeads have diameters in a range of about 20 µm to about 25 µm;
   (b) adding a portion of the mixture to a microfluidic chamber, thereby forming a bed comprising the microbeads with the cells distributed among the microbeads; and
   (c) perfusing the bed with a culture medium, wherein the osteocytes of the bed remain as osteocytes and pre-osteocytes of the bed develop into osteocytes and the perfusing is performed such that the osteocytes of the bed, the pre-osteocytes of the bed or both form the three-dimensional (3D) osteocyte network comprising the microbeads of the bed; and
   wherein the bed of microbeads is an environment effective
   (1) for cells to attach to the microbeads of the bed;
   (2) for cells to grow processes;
   (3) for cells to extend the processes to neighboring cells to form gap-junctions; and
   (4) to reduce osteocyte and pre-osteocyte proliferation in the interstitial space between adjacent microbeads and along surfaces of the microfluidic chamber.

2. The method of claim 1, wherein the microbeads of the bed have diameters such that the bed has an interstitial space between adjacent ones of the microbeads of the bed, wherein the interstitial space is of a size such that only one osteocyte or pre-osteocyte occupies the interstitial space.

3. The method of claim 1, wherein the cells are sourced from a species of animal, and the microbeads have diameters that are approximately the same size as a typical distance between osteocytes in a living animal of the species.

4. The method of claim 1, wherein the microbeads include biphasic calcium phosphate.

5. The method of claim 1, wherein the culture medium includes a biologically-active substance, and the method includes assessing an effect of the biologically-active substance on the development of the pre-osteocytes into osteocytes and the formation of the network of osteocytes among the microbeads of the bed.

* * * * *